United States Patent [19]

Snyder

[11] Patent Number: 4,757,821
[45] Date of Patent: Jul. 19, 1988

[54] OMNIDIRECTIONAL ULTRASONIC PROBE

[75] Inventor: Jonathan E. Snyder, Oklahoma City, Okla.

[73] Assignee: Corazonix Corporation, Oklahoma City, Okla.

[21] Appl. No.: 929,735

[22] Filed: Nov. 12, 1986

[51] Int. Cl.$^4$ ............................................. A61B 10/00
[52] U.S. Cl. ................................... 128/660; 128/663; 73/623
[58] Field of Search ................................. 128/660–663, 128/4; 73/861.25, 623, 642, 644

[56] References Cited

U.S. PATENT DOCUMENTS

| | | |
|---|---|---|
| Re. 31,377 | 9/1983 | Mylrea et al. ......................... 128/642 |
| 3,028,752 | 4/1962 | Bacon .................................. 73/623 X |
| 3,430,625 | 3/1969 | McLeod, Jr. ........................... 128/2.05 |
| 3,532,182 | 10/1970 | Bouyoucos ............................. 181/0.5 |
| 3,542,014 | 11/1970 | Peronneau ............................... 128/2 |
| 3,554,030 | 1/1971 | Peronneau ............................... 73/194 |
| 3,766,517 | 10/1973 | Fahrbach .............................. 340/3 D |
| 3,827,115 | 8/1974 | Bom ................................... 29/25.35 |
| 3,888,238 | 6/1975 | Meindl et al. .......................... 128/2 V |
| 3,901,077 | 3/1975 | McCarty et al. ....................... 73/194 A |
| 3,938,502 | 2/1976 | Bom .................................... 128/2 V |
| 3,951,136 | 4/1976 | Wall .................................. 128/2.06 E |
| 3,987,673 | 10/1976 | Hansen ............................... 73/194 A |
| 4,142,412 | 3/1979 | McLeod et al. ....................... 73/194 A |
| 4,237,729 | 12/1980 | McLeod et al. ....................... 128/663 X |
| 4,301,809 | 11/1981 | Pinchak ................................ 128/695 |
| 4,304,239 | 12/1981 | Perlin .................................. 128/642 |
| 4,304,240 | 12/1981 | Perlin .................................. 128/671 |
| 4,331,156 | 5/1982 | Apple et al. ........................... 128/688 |
| 4,349,031 | 9/1982 | Perlin .................................. 128/642 |
| 4,354,500 | 10/1982 | Colley et al. .......................... 128/663 |
| 4,354,501 | 10/1982 | Colley et al. .......................... 128/660 X |
| 4,361,044 | 11/1982 | Kupperman et al. ....................... 73/623 |
| 4,362,166 | 12/1982 | Furler et al. .......................... 128/670 |
| 4,369,794 | 1/1983 | Furler .................................. 128/671 |
| 4,407,293 | 10/1983 | Suarez, Jr. et al. .................... 128/660 |
| 4,409,986 | 10/1983 | Apple et al. ........................... 128/715 |
| 4,427,912 | 1/1984 | Bui et al. .............................. 310/322 |
| 4,476,872 | 10/1984 | Perlin .................................. 128/642 |
| 4,484,583 | 11/1984 | Graham ................................. 128/671 |
| 4,517,984 | 5/1985 | Perlin .................................. 128/642 |
| 4,532,933 | 8/1985 | Hokanson ............................... 128/660 |
| 4,541,434 | 9/1985 | Okodo .................................. 128/660 |
| 4,558,706 | 12/1985 | Nahado et al. .......................... 128/660 |

OTHER PUBLICATIONS

"An Esophageal Doppler Probe for Aortic Flow Velocity Monitoring," F. A. Duck, C. J. Hodson, and P. J. Tomlin, *Ult. in Med. and Biol.*, 1:233–241, Pergamon Press, Great Britain, 1974.

"Nontraumatic Aortic Blood Flow Sensing by Use of an Esophageal Probe," R. E. Daigle, C. W. Miller, M. B. Histand, F. D. McLeod, and D. E. Hokanson, *J. of App. Physiol.*, 38(6):1153–1160, Jun. 1975.

"Ultrasonic Transesophageal Measurement of Hemodynamic Parameters in Humans," M. K. Wells, M. B. Histand, J. T. Reeves, I. E. Sodal and H. P. Adamson, *Biomed. Sci. Instr.*, 14:7–12, 1978.

"Ultrasound Doppler and Echo Combined as a Noninvasive Flowmeter," M. B. Histand, R. A. Corace, and M. K. Wells, *Biomed. Sci. Instr.*, 17:73–78, 1981.

C. D. Side et al., "Non-Surgical Assessment of Cardiac Function," *Nature*, vol. 232, Jul. 30, 1971.

Kumar et al., "Non-Invasive Measurement of Cardiac Output During General Anesthesia by Continuous Wave Doppler Esophageal Probe: Comparison with Simultaneous Thermodilution Cardiac Output," *Anesthesiology*, vol. 53, No. 3A, Sep. 1985.

(List continued on next page.)

*Primary Examiner*—Francis J. Jaworski
*Attorney, Agent, or Firm*—Laney, Dougherty, Hessin & Beavers

[57] ABSTRACT

An omnidirectional ultrasonic probe, having specific application for connection to the distal end of an esophageal catheter, includes a support member upon which are coaxially mounted a transmitter member, a receiver member, and one or more acoustic reflector members. The acoustic reflector member or members reflect transmissions and receptions of ultrasonic signals along substantially parallel paths. The reflector members also provide omnidirectional reflection. Separate transmitter and receiver members are used in the preferred embodiments to facilitate continuous wave operation.

14 Claims, 2 Drawing Sheets

OTHER PUBLICATIONS

Colley et al., "Feasibility of Transesophageal Measurement of Cardiac Output During Surgery Using Doppler Ultrasound," *Anesthesiology,* vol. 63, No. 3A, Sep. 1985.

Freund et al., "A Comparison of Cardiac Output Techniques: Transesophageal Doppler Versus Thermodilution Cardiac Output During General Anesthesia in Man," *Anesthesiology,* vol. 63, No. 3A, Sep. 1985.

Wells et al., "Ultrasonic Transesophageal Measurement of Cardiac Output," 1978 Advances in Bioengineering Conference, San Francisco, Calif., Dec. 1978.

Histand et al., "Ultrasonic Pulsed Doppler Transoesophageal Measurement of Aortic Haemodynamics in Humans," *Ultrasonics,* Sep. 1979.

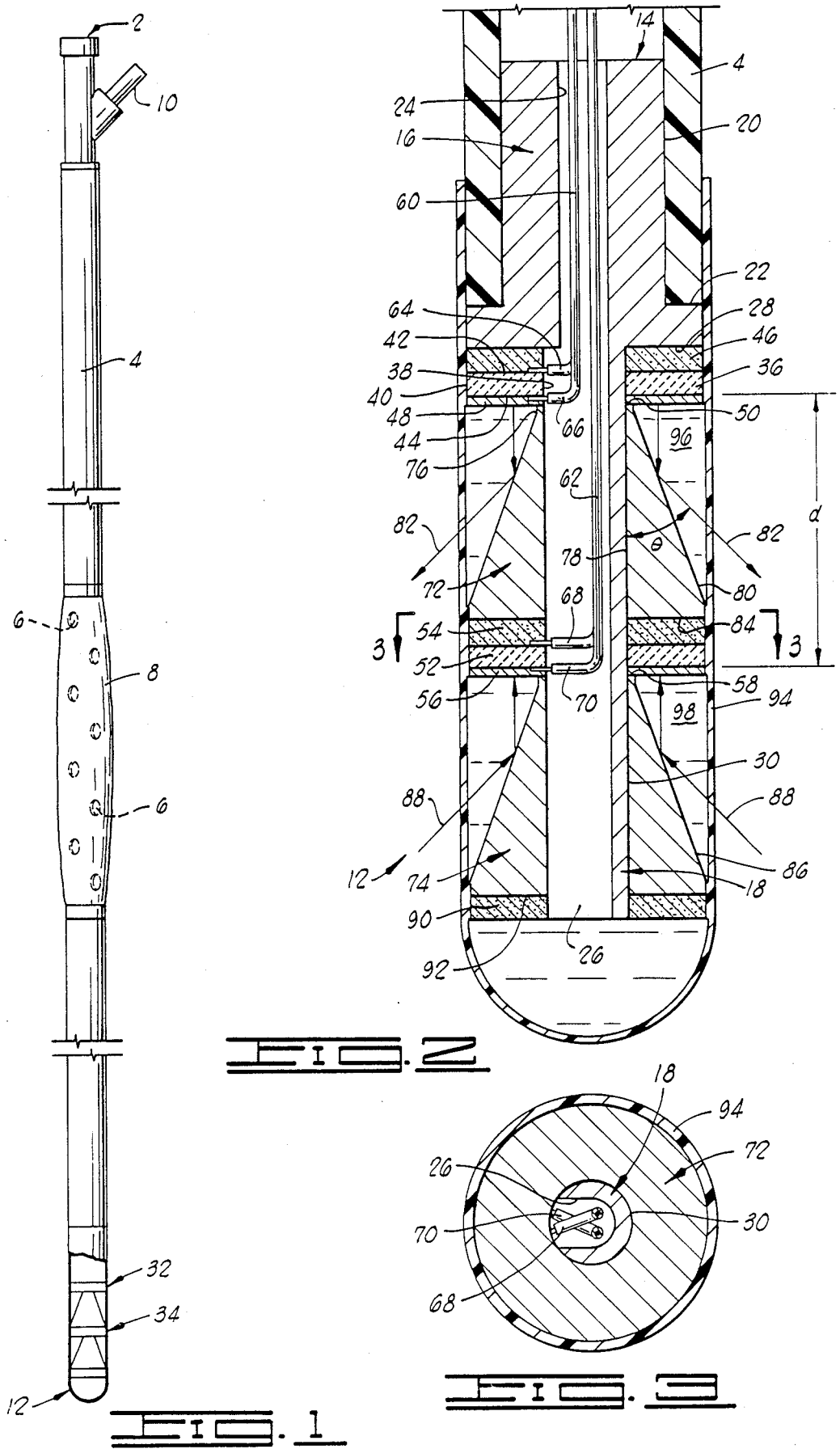

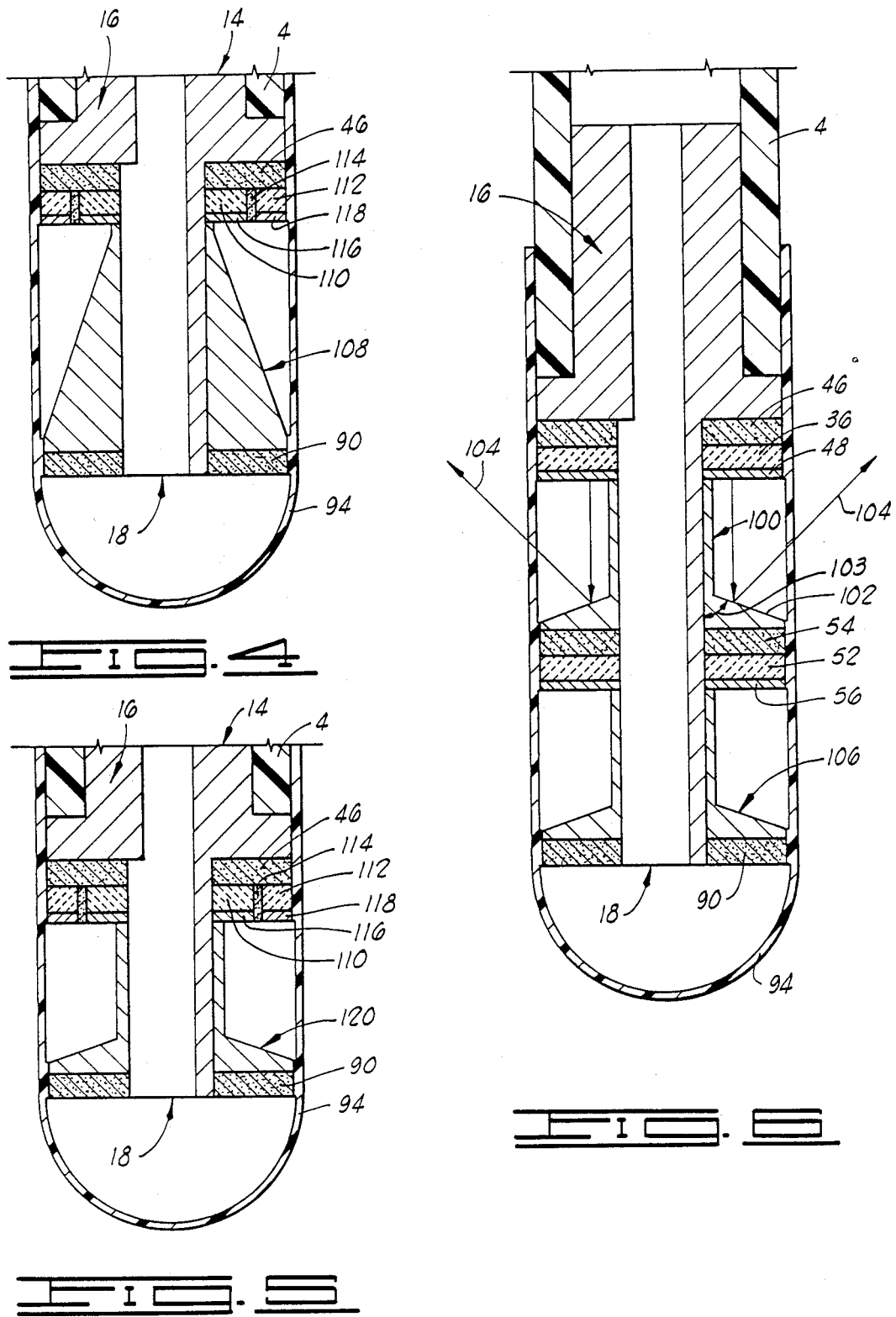

OMNIDIRECTIONAL ULTRASONIC PROBE

BACKGROUND OF THE INVENTION

This invention relates generally to ultrasonic probes for use inside the body of an animal (both human and non-human) and more particularly, but not by way of limitation, to apparatus to be removably placed in an esophagus at the end of a hollow catheter for use in detecting the velocity, by means of the Doppler effect, of an acoustic reflector within the range of the apparatus.

It has been described that the use of an esophageal probe fitted with an ultrasonic Doppler transducer is an ideal way of determining the velocity of blood flow in the descending aorta. See, F. A. Duck, C. J. Hodson, and P. J. Tomlin, "An Esophageal Doppler Probe for Aortic Flow Velocity Monitoring, " *Utl. in Med. and Biol.*, 1:233–241, Pregamon Press, Great Britain, 1974; R. E. Daigle, C. W. Miller, M. B. Histand, F. D. McLeod, and D. E. Hokanson, "Nontraumatic Aortic Blood Flow Sensing by Use of an Esophageal Probe," *J. of App. Physiol.*, 38(6):1153–1160, June 1975; M. K. Wells, M. B. Histand, J. T. Reeves, I. E. Sodal and H. P. Adamson "Ultrasonic Transesophageal Measurement of Hemodynamic Parameters in Humans," *Biomed. Sci. Instr.*, 14:7–12, 1978; and M. B. Histand, R. A. Corace, and M. K. Wells, "Ultrasound Doppler and Echo Combined as a Noninvasive Flowmeter," *Biomed. Sci. Instr.*, 17:73–78, 1981. Because the descending aorta passes through the chest cavity and enters the abdominal cavity parallel to the esophagus, the proximity of the esophagus and its orientation with respect to the descending aorta are ideal for the use of Doppler ultrasound to quantify noninvasively the blood flow velocity in this area. This provides, for example, a relatively simple technique for obtaining descending aorta blood flow velocity from a medical patient during surgery, which information can be used by the anesthesiologist in controlling the anesthetic agents given to the patient, thereby providing better controlled anesthesia.

Various types of ultrasonic transducers have been incorporated into or used with a standard esophageal stethoscope for this purpose. Some have used a pulsed ultrasonic signal; however, there have been some disclosures of at least the possibility of using a continuous wave ultrasonic signal (U.S. Pat. No. 4,354,501 to Colley et al.). With a continuous wave signal, the velocity is, of course, continuously measured; additionally, use of a continuous wave signal does not require any type of time delay to separate transmitted from received signals as might be necessary in a pulsed type of probe having a single transducer for both transmitting and receiving ultrasonic signals.

Some previous types of probes have also been directional in that the transmitted ultrasonic signal was directed within a sector rather than in a complete circumferential pattern. This requires that a person try to accurately aim the signal after the probe has been placed in the patient's esophagus, thereby creating a possibly significant chance of human error that would result in inaccurate data and thus, in the example of use by an anesthesiologist, improper administration of anesthetic agents.

Some types of probes have also been disclosed as utilizing reflective surfaces in reflecting the transmitted and received ultrasonic signals at angles relative to the longitudinal axis of the probe. This is disclosed in U.S. Pat. Nos. 4,142,412 and 4,237,729, both to McLeod et al. These patents, however, teach that the transmitted and received signals must be along non-parallel paths.

Despite the existence of ultrasonic transducers used with standard esophageal stethoscopes for obtaining the same type of data which preferred embodiments of the present invention are intended to obtain, an improved omnidirectional ultrasonic probe is needed to provide accurate operation with a design which is relatively simple and economical to manufacture and use. The design should allow the steering angle of the transmitted ultrasonic signal to be easily controlled or defined. The design should utilize a continuous wave ultrasonic signal to provide for constant monitoring; but such constant monitoring should be obtained with relatively little cross-talk between the continuous transmissions and receptions. The design should include acoustic isolation and matching elements and a liquid filled chamber for enhancing the transmission and reception of the ultrasonic signals. The design should also accomodate relatively easy insertion of the apparatus within the patient. More generally, the design should be one which works and which can be readily implemented.

SUMMARY OF THE INVENTION

The present invention meets the aforementioned needs by providing a novel and improved omnidirectional ultrasonic probe. In a specific application with a standard esophageal stethoscope, the invention can be used to measure blood velocity in the descending aorta. Such velocity measurements can be used, for example, by an anesthesiologist in controlling anesthetic agents given to a patient whose blood flow is being measured with the present invention. The present invention transmits and receives omnidirectionally and continuously via continuous wave ultrasonic signals so that no aiming and no time delay need be accomodated. The present invention also uses one or more reflective surfaces which may be designed at different angles to define different steering angles and thus to accomodate different longitudinal directions of ultrasonic transmission and reception; however, in the present invention both transmission and reception occur along substantially parallel reflective paths. By accomodating various reflection angles, the present invention has a flexibility which may allow it to be adapted to different uses; however, by requiring that transmission and reception occur along substantially parallel paths, the present invention has a relatively simplified, economical construction. The present invention provides this operation with relatively low cross-talk and with acoustic isolation and matching elements and a liquid filled chamber for enhancing the transmission and reception of the continuous wave signals. The present invention is designed to be relatively easily inserted into the subject in which the invention is to be used. Through these features the present invention provides a working probe which can actually be manufactured and used. Therefore, it is beleived that the present invention provides a probe which obtains advantages of the prior art and which further improves upon the prior art by obtaining such advantages in a relatively simplified, economical and practical construction.

The ultrasonic probe of the present invention, which may be used inside the body of an animal (which term includes humans), comprises a support member; transmitter means, connected to the support member, for transmitting within the body continuous wave ultrasonic signal during a test period; receiver means, connected to the support member, for receiving reflections of the continuous wave ultrasonic signal reflected from an acoustic reflector (e.g., blood flowing through descending aorta) of the body along a reception path; and acoustic reflector means, connected to the support member, for reflecting the continuous wave ultrasonic signal into the body from the transmitter member along a transmission reflection path and for reflecting to the receiver means the reflections of the continuous wave ultrasonic signal reflected from an acoustic reflector of the body along the reception path, wherein the acoustic reflector means is disposed relative to the transmitter means and the receiver means so that the transmission reflection path and the reception path are substantially parallel.

Therefore, from the foregoing, it is a general object of the present invention to provide a novel and improved omnidirectional ultrasonic probe. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 1 is a side elevational view of the present invention in the embodiment of an esophageal Doppler probe. The lower portion has been broken away to schematically illustrate an embodiment of the probe which is attached to an esophageal catheter drawn foreshortened to enable it to be more meaningfully illustrated in a single drawing.

FIG. 2 is a sectional elevational view of the probe and the lower end of the catheter taken along the longitudinal axis at the lower end of the assembly illustrated in FIG. 1.

FIG. 3 is a sectional view taken along line 3—3 shown in FIG. 2. FIG. 4 is a sectional view similar to FIG. 2, but illustrating another embodiment of the invention.

FIG. 5 is sectional view similar to those shown in FIGS. 2 and 4, but illustrating a further embodiment of the invention.

FIG. 6 is a sectional view similar to those of FIGS. 2, 4 and 5, but illustrating still another embodiment of the invention.

DETAILED DESCRIPTION OF THE PREFERRED EMBODIMENTS

In FIG. 1 there is shown a hollow catheter 2 made of an elongated flexible, smooth plastic tubular element 4 to be inserted into an esophagus, for example, in a conventional manner. It is contemplated that the present invention may be used in environments other than an esophagus, such as in other internal tubular parts of an animal. Intermediate the ends of the element 4 there is a perforated section having a plurality of perforations 6. The perforations 6 are protectively housed in a sleeve 8 (such as a heat shrinkable one) acting not only as a seal for preventing liquid from entering the perforations 6, but also as a diaphragm or membrane through which are aurally detectable sounds are communicated for passage through the perforations 6 up the hollow interior of the tubular element 4 to a stethoscopic receiving instrument, such as a conventional stethoscope (not shown) connected to an adapter 10 defining part of a bifurcated upper, or proximal, end of the catheter 2. In describing the preferred embodiment of the present invention reference will be made by way of example to its use in a human esophagus so that examples of the aurally detectable sounds which can be communicated through the membrane 8 up to a stethoscope connected to the adapter 10 are sounds emanating from the heart and lungs near which the esophagus passes; however, as stated above it is contemplated that the present invention has utility in other applications.

Connected to the lower, or distal, end of the catheter 2 is a probe 12 constructed in accordance with the present invention. In the preferred embodiment the probe 12 is an ultrasonic signal generating and receiving transducer assembly having one of the four particular embodiments depicted in FIGS. 1-6. One embodiment will be described with reference to FIGS. 1-3, and a modification thereof will be described with reference to FIG. 6. A further embodiment will be described with reference to FIG. 4, and a modification thereof will be described with reference to FIG. 5. Like elements of these different embodiments are indicated by the same reference numerals.

Broadly, each of these embodiments comprises a support member; transmitter means, connected to the support member, for transmitting within the body a continuous wave ultrasonic signal during a test period; receiver means, connected to the support member, for receiving reflections of the continuous wave ultrasonic signal reflected along a reception reflection path from an acoustic reflector of the body into which the probe is placed; and acoustic reflector means, connected to the support member, for reflecting the continuous wave ultrasonic signal into the body from the transmitter means along a transmission reflection path and for reflecting to the receiver means the reflections of the continuous wave ultrasonic signal reflected from an acoustic reflector of the body along the reception reflection path, wherein the acoustic reflector means is disposed relative to the transmitter means and the receiver means so that the transmission reflection path and the reception reflection path are substantially parallel. As used herein, "transmission reflection path" and "reception reflection path" mean the three-dimensional beam patterns defined or traversed by the ultrasonic energy transmitted and received by the present invention, respectively. In the preferred embodiment these patterns are established circumferentially around the probe 12 because the probe 12 operates omnidirectionally. As used herein the "acoustic reflector" of the body from which reflections are received along a "reception reflection path" refers to something within the range of the probe 12 which can reflect the transmitted continuous wave ultrasonic signal. In the specific example of monitoring descending aorta blood flow velocity, an "acoustic reflector" would be the moving blood stream in the descending aorta, or more particularly, the moving blood cells. Such an "acoustic reflector" of the preferred embodiment is one external of the probe 12 as distinguished from the acoustic reflector means which is an element of the present invention.

In the embodiment shown in FIGS. 1-3, the support member is generally identified by the reference numeral 14. This member 14 is an integral piece having two portions defined as a hub 16 and a shaft 18 extending axially from the hub 16. The member 14 is made of any suitable substance (e.g., aluminum, stainless steel, plastic).

The hub 16 has a cylindrical outer surface 20 having a diameter which is suitable for allowing the hub 16 to fit into the distal end of the catheter 2. This diameter can be such that the hub 16 and the tubular element 4 of the catheter 2 frictionally engage with each other to provide a holding force for holding the probe 12 on the catheter 2. Extending radially outwardly from the surface 20 is a circumferential flange 22 which abuts the lower end of the catheter 2 when the probe 12 is attached to it. The hub 16 has a cylindrical inner surface 24 defining an axial opening or channel (also referred to by the reference numeral 24) through it.

The opening or channel 24 communicates with an axially aligned opening or slot defined through the shaft 18 by a U-shaped inner surface 26. The shaft 18 extends axially from a lower annular surface 28 defining the lower extent of the hub 16 and its flange 22. Intersecting this surface 28 is a U-shaped outer surface 30 of the shaft 18.

In addition to connecting the probe 12 with the catheter 2, the support member 14 provides mechanical or structural support for the remaining elements of the invention, two of which elements are the transmitter means and the receiver means. In FIG. 1, the transmitter means is generally identified by the reference numeral 32, and the receiver means is generally identified by the reference numeral 34. The relationship of these two means is depicted with the transmitter means 32 above the receiver means 34; however, it is contemplated that the element 34 could, in fact, be operated as the transmitter means with the element 32 being operated as the receiver means because the constructions of these two portions of the illustrated embodiment are identical. For purposes of convenience, the upper one of these elements will be referred to as the transmitter means and the lower as the receiver means, but with the understanding that such designations could be reversed and remain within the scope of the present invention.

The particular construction of the embodiment of the transmitter means 32 of the embodiment depicted in FIGS. 1–3 is best shown in FIG. 2. In this construction the transmitter means 32 includes a piezoelectric ceramic transducer 36. The transducer 36 has an annular configuration with an axial opening or hole defined by a longitudinal surface 38 having a diameter sufficient so that the shaft 18 can pass through the opening. The transducer 36 has a cylindrical outer surface 40 which intersects axially spaced annular surfaces 42, 44 of the transducer 36. The transducer 36 is mounted on the shaft 18 near its end adjacent the hub 16 where the outer surface 30 of the shaft 18 intersects the surface 28 of the hub 16. The transducer 36 is poled and plated so that it operates in an axial thickness mode whereby ultrasonic signals are propagated parallel to the longitudinal axis of the probe 12. This is accomplished by suitably plating the ceramic body of the transducer 36, such as by a silk screen process for depositing silver on the ceramic or by a vacuum deposit process for depositing gold on the ceramic, as known to the art. In its contemplated preferred use in a medical environment, the transducer 36 is constructed so that it is resonant at a suitable frequency or frequencies within a range between approximately 500 kHz and 20 MHz.

In coaxially mounting the transducer 36 on the shaft 18, the transducer 36 is associated with a layer 46 of acoustic isolation material. The layer 46 has an annular shape similar to the shape of the transducer 36. The layer 46 is disposed or retained between the annular surface 42 of the transducer 36 and the annular surface 28 of the hub 16 of the support member 14. The acoustic isolation material of which the layer 46 is comprised can be of any suitable material known to the art. One example is a foamed cellular plastic; another example is a layer of air. In general, the material should be of a type which prevents coupling of acoustic energy produced by the transducer 36 into the support member 14 or the subsequently described acoustic reflector of the probe 12. Preventing such coupling will increase the performance of the transducer 36 and reduce acoustic crosstalk.

Another component shown used with the transducer 36 is a one-quarter wavelength matching member 48 also having an annular shape. The member 48 is made of a suitable material such as plastic or metal or otherwise as known to the art for improving the performance of the transducer 36 by increasing the quality factor Q of the resonant circuit of which the transducer 36 forms a part in a manner as known to the art and further described hereinbelow. The annular matching member 48 is bonded by a suitable material to the transducer 36 and is otherwise supported against an annular surface 50 of part of the acoustic reflector means more particularly described hereinbelow. More than one matching member can be used here and where other similar, subsequently described members are used.

The receiver means 34 of the embodiment shown in FIG. 2 is constructed identically to the transmitter means 32. In this regard, the receiver means 34 includes an annular piezoelectric ceramic transducer 52 coaxially mounted on the shaft 18, which also places the transducer 52 coaxially with the transducer 36. The transducer 52 is, however, disposed near the opposite end of the portion of the reflector means having the end surface 50 so that the transducer 52 is spaced longitudinally from the transducer 36 by a longitudinal distance d having particular significance as further described hereinbelow.

In the same manner as with the transducer 36, associated with the transducer 52 are an annular layer 54 of acoustic isolation material and an annular one-quarter wavelength matching member 56 bonded to the transducer 52 and supported adjacent an upper surface 58 of another portion of the acoustic reflector means of the embodiment shown in FIGS. 1–3.

For communicating an energizing electrical voltage or current to the transmitter transducer 36, the preferred embodiment shown in FIG. 2 includes a coaxial pair 60 of electrical conductors. Connected to the receiver transducer 52 for communicating an electrical voltage or current generated by the transducer 52 in response to ultrasonic signals obtained as reflections of ultrasonic signals generated by the transducer 36 are two electrical conductors of a coaxial pair 62. The two conductors of the pair 60 are connected across the axial thickness of the transducer 36 so that one conductor is connected to the surface 42 and the other conductor is connected to the surface 44 of the transducer 36. These connections are made so that radial extensions 64, 66 of the conductors extend through substantially the same diametric plane. This is better illustrated in FIG. 3 which shows radial portions 68, 70 of the conductors of the coaxial pair 62, which pair is connected to the receiver transducer 52. As drawn in FIG. 3, the radial extensions 68, 70 are not exactly the same diametric plane, which would perpendicular to the surface of the drawing, but are intended as being shown to be offset by only a few degrees. This construction facilitates passage of the wires into the axial channel extending through the support member 14.

As the FIG. 2 embodiment is described with the transducer 36 being the transmitter and the transducer 52 being the receiver, then the conductors of the pair 60 are used to activate the transducer 36 to propagate a continuous wave acoustic signal which, because of the construction and structural positioning of the transducer 36, propagates the continuous wave acoustic signal parallel to the shaft 18 of the support member 14. In accordance with this assignment of transmission and reception designations, the conductors of the pair 62 are connected so that it is through these electrical conductors that the transducer 52 transmits electrical signals in response to reflections of the continuous wave acoustic signal reflected from an acoustic reflector external to the probe 12 (e.g., the descending aorta blood flow stream) and received by the transducer 52.

The acoustic reflector means of the embodiment particularly shown in FIG. 2 includes two acoustic reflector members 72, 74, the reflector member 72 being associated with the transmitter means 32 and the reflector member 74 being associated with the receiver means 34 for the exemplary designation thereof used herein. The reflector members 72, 74 are made of any suitable acoustic energy-reflective substance known to the art, such as aluminum or plastic. The reflector member 72 reflects the continuous wave acoustic energy away from the probe 12 at a steering angle $\theta$ measured relative to the longitudinal axis of the probe 12; the reflector member 74 receives acoustic reflections from the external acoustic reflector within a path also having a steering angle $\theta$ relative to the longitudinal axis of the probe 12 in the preferred embodiment and reflects them towards the receiver means 34.

The reflector member 72 is mounted coaxially on the shaft 18 and coaxially relative to the transducers 36, 52. The reflector member 72 has the annular surface 50 at its upper end near the transducer 36 and, in particular, adjacent the lower surface of the one-quarter wavelength matching member 48. Extending longitudinally from the outer perimeter of the surface 50 is a cylindrical surface 76, in combination with which the surface 50 and part of a cylindrical inner surface 78 define a cylindrical neck portion of the reflector member 72. The surface 78 extends in axial alignment on through the longitudinal center of a conical frustum portion of the reflector member 72.

The exterior of the conical frustum portion is defined by an outer oblique surface 80. The surface 80 is disposed relative to the transducer 36 so that the continuous wave acoustic signal propagated from the transducer 36 when it is activated is reflected along a circumferential, or omnidirectional, transmission reflection path oblique to the shaft 18. This transmission reflection path, or beam pattern, extends circumferentially around the entire perimeter of the probe 12 as intended to be indicated in the two dimensions of FIG. 2 by arrows 82. These arrows 82 depict that the 360° beam pattern forms an oblique angle $\theta$ with the longitudinal axis of the probe 12, which angle is the aforementioned steering angle. In the FIG. 2 embodiment this angle is a downwardly directed acute angle so that the arrows 82 are directed angularly downward but laterally from the probe 12. In the preferred embodiment the angle $\theta$ equals approximately 45° which is obtained by forming the surface 80 at an angle of approximately 22.5° relative to the longitudinal axis of the reflector member 72 (and thus also relative to the longitudinal axis of the probe 12).

The reflector member 72 terminates at its lower end in an annular surface 84 adjacent which the layer 54 of acoustic insulation material associated with the transducer 52 is disposed.

The reflector member 74 is constructed identically to the reflector member 72 in the illustrated preferred embodiment. The reflector member 74 is disposed below the transducer 52 (and thus on the opposite side of the transducer 52 from the reflector member 72) so that reflections of the continuous wave acoustic signal which are reflected from, for example, an external acoustic reflector outside the esophogus are reflected by an oblique surface 86 of the member 74 to define further reflections to which the transducer 56 is responsive. In the illustrated preferred embodiment the oblique angle at which the surface 86 is disposed is equal to the angle of the surface 80 [i.e., $(\frac{1}{2})\theta$].

It is to be noted that some small deviation from equality of the angles at which the surfaces 80, 86 are disposed can be accommodated in the present invention; however, it is an important feature of the present invention that the angles of these surfaces relative to the longitudinal axis always be at least substantially equal with only a few degrees of variation being permitted so that the relatively simple and economical construction advantages of the present invention are obtained.

Because the angles of the surfaces 80, 86 are substantially equal (which includes being of equal angle as well as small deviations therefrom) and further because the acoustic reflector members 72, 74 are coaxially mounted on the shaft 18 so that the shaft 18 extends through the axial openings of both reflector members, the outer oblique surfaces 80, 86 may be said to be substantially parallel. Therefore, an incoming reflection which is received within a reception reflection path indicated by arrows 88 is substantially parallel to a transmitted ultrasonic signal propagated and reflected within the path represented by the arrows 82. When the surfaces 80, 86 are constructed to be truly parallel as illustrated in FIG. 2, such true parallelism can be accommodated through the diffraction, or spread of the beam patterns (or responses), of the transmitted and received signals (or their transducers) so that such true or exact parallelism may be maintained despite the longitudinal spacing between the surfaces 80, 86. The amount of deviation from such exact parallelism which may be accommodated in the present invention, such as for focusing the transmit and receive beam patterns, and thus the limits of "substantially parallel" as including both exact parallelism and such deviation and as used in this context, is based on the following equation derived from the law of cosines:

$$\phi° = \arccos\left[\frac{z^2 - (d/2)^2}{\sqrt{z^4 + (d/2)^4 + (dz)^2(\frac{1}{2} - \cos^2\theta)}}\right]$$

where $\theta$ is the desired or nominal base steering angle in degrees as previously defined, d is the previously defined axial spacing in millimeters between corresponding surfaces of the transducers 36, 52, and z is the distance in millimeters that the acoustic reflector target to be detected by the reflected ultrasonic signal is spaced from the probe 12 (measured from the midpoint of d to the target). The angle $\phi$ represents the maximum deviation from true parallel between the resultant transmit steering angle and the resultant receive steering angle. These resultant steering angles are obtained by constructing one or both of the reflector members 72, 74 so that the maximum deviation from true parallel between the surfaces 80, 86 is $(\frac{1}{2})(\phi)$. By way of example, for a nominal steering angle $\theta = 45°$ and suitable dimensions for d and z, $\phi$ could be approximately 14°; therefore, the surfaces 80, 86 would be constructed to be offset approximately 7° from each other, such as could be done by changing the slope of the surface 80 approximately 3.5° in one direction relative to the longitudinal axis of the probe 12 and by changing the slope of the surface 86 approximately 3.5° in the other direction relative to the longitudinal axis of the probe 12.

The construction of the embodiment shown in FIG. 2 also includes a layer 90 of suitable acoustic isolation material disposed adjacent a lower annular surface 92 of the reflector member 74. The layer 90 is used at the bottom of the illustrated assembly to prevent acoustic energy from being transmitted in a direction parallel to the longitudinal axis of the probe 12.

Encapsulating or enclosing the transmitter means 32, the receiver means 34, the reflector members 72, 74, the various layers of acoustic isolation material, and the one-quarter wavelength matching members is a relatively thin, elongated sleeve 94 made of a suitable flexible plastic for protecting the internal components and for facilitating insertion of the probe 12 into the esophagus. The sleeve 19 also defines a sheath or casing for containing liquid means for enhancing the transmission of acoustic energy through cavities 96, 98 defined between the reflector members 72, 74 and the facing portions of the inner surface of the sleeve 94. In the preferred embodiment the liquid means is any suitable water-based or oil-based liquid for conducting ultrasonic energy with minimal distortion and attenuation. The sleeve 94 is attached to the tubular element 4 of the catheter 2 by a suitable thermoplastic bonding technique. As shown in FIG. 2, the sleeve 94 also engages or connects with the outer cylindrical surface at the end of the flange 22 of the hub 16.

Another embodiment of the present invention is partially shown in FIG. 6. This embodiment is identical to the embodiment shown in FIG. 1 except for the specific shape of the two reflector members. In the FIG. 6 embodiment a reflector member 100 has an oblique surface 102 defined at an angle 103 of approximately 67.5° so that the omnidirectional transmission reflection path defined by axially parallel propagations reflecting off the surface 102 extends at an upwardly aimed angle of approximately 45° relative to the longitudinal axis of the embodiment of the probe shown in FIG. 6. This omnidirectional transmission reflection path is identified in the two-dimensions of FIG. 6 by arrows 104.

The reflector member 100 is also distinguishable from the corresponding reflector member 72 in the FIG. 2 embodiment by having a longer neck portion. The particular length of this longer neck portion is selected so that the transmission reflection path allows a substantial portion of the propagated ultrasonic energy to be reflected out of the probe 12 rather than being reflected back toward the transducer 36 within the encased boundary of the probe depicted in FIG. 6.

A reflector member 106 is constructed identically (or within the deviation based on 100° previously defined) to the reflector member 100 but spaced longitudinally downwardly therefrom for use with the receiver transducer 52 of the FIG. 6 embodiment.

The embodiment of the present invention shown in FIG. 4 has several elements similar to those shown in FIG. 2 as indicated by like reference numerals. The FIG. 4 embodiment, however, has only a single reflector member 108 which is identical to either of the reflector members 72, 74 shown in FIG. 2. Only one reflector member 108 is needed in the FIG. 4 embodiment because it provides the same reflective surface for both the transmission reflection path and the reception reflection path; therefore, the oblique surface of the reflector member 108 reflects transmitted and received acoustic signals along the same angle of reflection. Only one such reflecting surface is needed because the transmitter means the receiver means of the FIG. 4 embodiment are defined by two concentrically located transducers 110, 112. As with the previously described embodiments, the transducer 110 can be used as either the transmitter or the receiver and the transducer 112 can be used as either the receiver or transmitter, respectively.

To acoustically isolate the transducers 110, 112, the FIG. 4 embodiment includes an annular layer 114 of acoustic isolation material disposed radially between the transducers 110, 112. The layer 114 alone is disposed between two concentrically related one-quarter wavelength matching members 116, 118 attached to the transducers 110, 112, respectively.

The embodiment of FIG. 5 is constructed identically to the embodiment shown in FIG. 4 except the FIG. 5 embodiment incorporates a single reflector member 120 having a shape identical to the shape of the reflector members 100, 106 shown in FIG. 6.

Any of the embodiments shown in FIGS. 4-6 may be used by attaching it to the catheter 2 as the probe 12 in place of the particular embodiment thereof represented in FIG. 1. Additionally, each of the embodiments shown in FIGS. 4-6 has its transducers suitably connected to electrical conductors which are to be connected to electrical circuitry outside the catheter 2 in a manner as known to the art and the same as for the embodiment of FIGS. 1-3.

In operation, the selected embodiment is attached at the end of the catheter 2 by inserting the hub of the probe into the distal end of the tubular element 4 and bonding the sleeve of the probe with the outer surface of the tubular element 4. This assembly is then lowered into the esophagus (in the specific example) in a conventional manner, and the electrical conductors extending from the probe out of the proximal end of the catheter 2 are connected to suitable circuitry for controlling the transmission of ultrasonic signals from the transmit transducer and for receiving reflections of these signals received by the receive transducer. An example of such circuitry is described in U.S. Pat. No. 4,608,993 to Albert issued Sept. 2, 1986, and incorporated herein by reference. In the preferred embodiment, continuous wave ultrasonic transmissions occur continuously throughout the time a test, such as the monitoring of moving blood cells, is being conducted; this permits constant monitoring to be obtained.

With the catheter/probe assembly so emplaced and connected, ultrasonic signals can be transmitted and received and analyzed in accordance with the Doppler effect to determine the velocity in accordance with the Doppler effect to determine the velocity of the target external acoustic reflector, such as the blood stream flowing through the descending aorta located within a few centimeters of the esophagus in which the catheter/probe assembly is located in this exemplary environment. In a human, this distance is approximately twenty to forty millimeters; this distance defines, for this particular example, the range z referred to hereinabove with reference to the parallelism angle $\phi$ pertinent to the embodiments shown in FIGS. 2 and 6.

The information derived from this monitoring can be used for any suitable purpose, such as by an anesthesiologist in controlling the anesthetic agents given to a patient undergoing surgery and having the present invention placed in his or her esophagus.

Thus, the present invention is well adapted to carry out the objects and attain the ends and advantages mentioned above as well as those inherent therein. While preferred embodiments of the invention have been described for the purpose of this disclosure, changes in the construction and arrangement of parts can be made by those skilled in the art, which changes are encompassed within the spirit of this invention as defined by the appended claims.

What is claimed is:

1. An apparatus to be removably placed in an esophagus at an end of a hollow catheter for use in detecting, by means of the Dopper effect, the velocity of an acoustic reflector target, said apparatus comprising:
   a support member, including:
      hub means for connecting with the hollow catheter; and
      a shaft extending axially from said hub means;
   a first piezoelectric transducer mounted on the end of said shaft adjacent said hub means;
   a first acoustic reflector member including a first end and a second end, said first acoustic reflector member mounted on said shaft with said first end of said first acoustic reflector member near said first piezoelectric transducer;
   a second piezoelectric transducer mounted on said shaft near said second end of said first acoustic reflector member;
   a second acoustic reflector member mounted on said shaft with said second piezoelectric transducer in between said first acoustic reflector member and said second acoustic reflector member; and
   wherein:
      each of said first and second acoustic reflector members includes:
         a cylindrical neck portion having an inner cylindrical surface defining an axial opening; and
         a conical frustum portion having an inner cylindrical surface defining an axial opening extending in axial alignment with said axial opening through said cylindrical neck portion, and said conical frustum portion further having an outer oblique surface; and
      said first and second acoustic reflector members are coaxially mounted on said shaft ot said support member so that said shaft extends through said axial openings of said reflector members and so that said outer oblique surfaces of said conical frustum portions of said reflector members are parallel.

2. An apparatus as defined in claim 1, further comprising:
   a first layer of acoustic isolation material, said first layer disposed between said hub means and said first piezoelectric transducer;
   a first one-quarter wavelength matching member, said first matching member disposed between said first piezoelectric transducer and said first acoustic reflector member;
   a second layer of acoustic isolation material, said second layer disposed between said first acoustic reflector member and said second piezoelectric transducer;
   a second one-quarter wavelength matching member, said second matching member disposed between said second piezoelectric transducer and said second acoustic reflector member; and
   a third layer of acoustic isolation material, said third layer disposed adjacent the end of said second acoustic reflector member opposite said second piezoelectric transducer.

3. An apparatus as defined in claim 1, wherein:
   said hub means and said shaft include an axial opening extending therethrough; and
   said apparatus further comprises a first pair of electrical conductors connected to said first piezoelectric transducer and extending through said axial opening of said hub means and said shaft, and a second pair of electrical conductors connected to said second piezoelectric transducer and extending through said axial opening of said hub means and said shaft, so that a selectable one of said first and second piezoelectric transducers is activated to propagate a continuous wave acoustic signal parallel to said shaft of said support member and so that the other of said first and second piezoelectric transducers transmits electrical signals through its respective pair of electrical conductors in response to reflections of said continuous wave acoustic signal reflected from the acoustic reflector target.

4. An apparatus as defined in claim 1, further comprising:
   a casing connected to said hub means and extending around said first and second piezoelectric transducers and said first and second acoustic reflector members so that cavities are defined between said casing and said first and second acoustic reflector members; and
   liquid means, disposed in said cavities, for enhancing the transmission of acoustic energy through said cavities.

5. An ultrasonic probe for use inside the body of an animal, comprising:
   transmitter means for transmitting within the body an ultrasonic signal;
   receiver means for receiving reflections of said ultrasonic signal reflected from an acoustic reflector of the body;
   a first acoustic reflector member connected to said transmitter means and including first surface means for reflecting into the body said ultrasonic signal from said transmitter means; and
   a second acoustic reflector member connected to said receiver means and including second surface means for reflecting to said receiver means said reflections of said ultrasonic signal reflected from an acoustic reflector of the body, said second acoustic reflector member disposed relative to said first acoustic reflector member so that said first surface means and said second surface means are substantially parallel.

6. A probe as defined in claim 5, wherein:

said first surface means includes an outer oblique surface of a first conical frustum; and said second surface means includes an outer oblique surface of a second conical frustum.

7. A probe as defined in claim 6, wherein:

said first conical frustum includes a longitudinal center axis; and said probe further comprises means for supporting said second conical frustum coaxially with said longitudinal center axis of said first conical frustum.

8. A probe as defined in claim 6, wherein:

said first acoustic reflector member further includes a first cylindrical neck, said first cylindrical neck extending from an end of said first conical frustum; and said second acoustic reflector member further includes a second cylindrical neck, said second cylindrical neck extending from an end of said second conical frustum.

9. A probe as defined in claim 5, wherein:

said first acoustic reflector member includes a longitudinal center axis;

said first surface means of said first acoustic reflector member is disposed so that said first surface means reflects said ultrasonic signal at a nominal steering angle $\theta$ relative to said longitudinal center axis;

said transmitter means and said receiver means include corresponding surfaces spaced axially relative to said longitudinal center axis a distance of d millimeters;

said distance d has a midpoint located between said transmitter means and said receiver means and spaced from the acoustic reflector of the body a distance of z millimeters when said probe is positioned inside the body; and said substantially parallel first and second surface means are characterized by being within the range of parallelism between 0° deviation from true parallel and $(\frac{1}{2})(\phi)°$ deviation from true parallel, wherein $$\phi° = \arccos\left[\frac{z^2 - (d/2)^2}{\sqrt{z^4 + (d/2)^4 + (dz)^2(\frac{1}{2} - \cos^2\theta)}}\right].$$

10. An ultrasonic probe for use inside the body of an animal, comprising:

an elongated support member having a longitudinal center axis;

an annular first transducer having a hole through which said support member extends;

a first acoustic reflector member including a first conical frustum portion through which said support member extends, said first conical frustum portion of said first acoustic reflector member having an exterior defined by an outer oblique surface disposed at a first angle, by which a nominal steering angle $\theta°$ different from said first angle is defined, relative to said longitudinal center axis;

an annular second transducer having a hole through which said support member extends so that said second transducer is mounted on said support member with a distance of d millimeters between corresponding locations of said first and second transducers;

a second acoustic reflector member including a second conical frustum portion through which said support member extends, said second conical frustum portion of said second acoustic reflector member having an exterior defined by an outer oblique surface disposed at a second angle relative to said longitudinal center axis, wherein the difference between said first and second angles is not greater than $(\frac{1}{2})(\phi)°$ where $$\phi° = \arccos\left[\frac{z^2 - (d/2)^2}{\sqrt{z^4 + (d/2)^4 + (dz)^2(\frac{1}{2} - \cos^2\theta)}}\right],$$

and where z = the distance in millimeter that an acoustic reflector target of the body is spaced from the midpoint of the distance d between said first and second transducers.

11. A probe as defined in claim 10, wherein:

said first acoustic reflector member further includes a first cylindrical neck portion, said first cylindrical neck portion extending from an end of said first conical frustum portion towards said first transducer; and said second acoustic reflector member further includes a second cylindrical neck portion, said second cylindrical neck portion extending from an end of said second conical frustum portion towards said second transducer.

12. An ultrasonic probe for use inside the body of an animal, comprising:

an elongated support member having a longitudinal center axis;

a single pair of concentric transducers, including:

an annular first transducer mounted around said support member so that said first transducer is coaxial with said longitudinal center axis; and an annular second transducer mounted around said first transducer so that said second transducer is coaxial with said longitudinal center axis and said first transducer is concentric within said second transducer; and a single acoustic reflector member mounted on said support member coaxial with said longitudinal center axis, said single acoustic reflector member including a single exterior oblique surface extending around said support member and extending obliquely relative to said longitudinal center axis.

13. A probe as defined in claim 12, wherein said single acoustic reflector member further includes a cylindrical neck portion extending from an end of said oblique surface towards said single pair of concentric transducers.

14. A probe as defined in claim 12, wherein:

said support member includes:

a shaft on which said single pair of concentric transducers and said single acoustic reflector member are mounted; and a hub including an annular surface extending from said shaft; and said probe further comprises:

a first layer of acoustic isolation material, said first layer disposed between said annular surface of said hub and both of said first and second transducers;

a first one-quarter wavelength matching member, said first matching member disposed adjacent said first transducer and around said shaft of said support member so that said first transducer is in between said first matching member and said first layer of acoustic isolation material;

a second one-quarter wavelength matching member, said second matching member disposed adjacent said second transducer and around said first matching member so that said second transducer is in between said second matching member and said first layer of acoustic isolation material and so that said first matching member is concentric within said second matching member; and a second layer of acoustic isolation material, said second layer disposed in between said first and second transducer and in between said first and second matching members.

* * * * *

UNITED STATES PATENT AND TRADEMARK OFFICE
CERTIFICATE OF CORRECTION

PATENT NO. : 4,757,821

DATED : July 19, 1988

INVENTOR(S) : Jonathan E. Snyder

It is certified that error appears in the above-identified patent and that said Letters Patent are hereby corrected as shown below:

In Column 2, lines 20-21, delete "accomodate" and insert -accommodate-.

In Column 2, line 39, delete "accomodated" and insert -accommodated.-

In Column 2, line 42, delete "accomodate" and insert -accommodate-.

In Column 2, line 46, delete "accomodating" and insert -accommodating-.

In Column 3, line 2, after "body" insert -a-.

In Column 3, line 7, after "reception" insert -reflection-.

In Column 3, line 14, after "reception" insert -reflection-.

In Column 3, line 17, after "reception" insert -reflection-.

In Column 3, line 41, after "shown in Figure 2." start a new paragraph with "Fig. 4 is a".

In Column 5, line 54, after "hub 16." start a new paragraph with "The transducer 36".

In Column 6, line 68, after "not" insert -in-.

In Column 8, line 17, delete "esophogus" and insert "esophagus".

In Column 10, line 2, delete "100°" and insert - $\theta°$ -.

UNITED STATES PATENT AND TRADEMARK OFFICE
CERTIFICATE OF CORRECTION

PATENT NO. : 4,757,821

DATED : July 19, 1988

INVENTOR(S) : Jonathan E. Snyder

It is certified that error appears in the above-identified patent and that said Letters Patent is hereby corrected as shown below:

In Column 10, line 19, after "means" first occurrence insert --and--.
In Column 16, line 8, delete "transducer" and insert --transducers--.

Signed and Sealed this

Fourth Day of October, 1988

Attest:

DONALD J. QUIGG

*Attesting Officer*    *Commissioner of Patents and Trademarks*